United States Patent [19]

Urbas

[11] 4,444,881

[45] Apr. 24, 1984

[54] RECOVERY OF ORGANIC ACIDS FROM A FERMENTATION BROTH

[75] Inventor: Branko Urbas, Darien, Ill.

[73] Assignee: CPC International Inc., Englewood Cliffs, N.J.

[21] Appl. No.: 507,812

[22] Filed: Jun. 27, 1983

Related U.S. Application Data

[63] Continuation-in-part of Ser. No. 314,627, Oct. 26, 1981, Pat. No. 4,405,717.

[51] Int. Cl.$^3$ .......................... C12P 7/48; C12P 7/52; C12P 7/56
[52] U.S. Cl. .................... 435/139; 435/141; 435/142; 203/15; 203/38; 562/513; 562/584; 562/589; 562/606
[58] Field of Search .................. 435/139, 141, 142; 203/15, 38; 562/513, 584, 589, 606

[56] References Cited

U.S. PATENT DOCUMENTS

| | | | |
|---|---|---|---|
| 2,143,359 | 1/1939 | Daly et al. | 435/139 |
| 3,202,705 | 8/1965 | Powell et al. | 562/589 |
| 3,944,606 | 3/1976 | Rieger et al. | 562/584 |
| 4,100,189 | 7/1978 | Mercier | 562/608 |
| 4,275,234 | 6/1981 | Baniel et al. | 562/584 |
| 4,282,323 | 8/1981 | Yates | 435/140 |
| 4,334,095 | 6/1982 | Baniel | 562/589 |

*Primary Examiner*—Wilbur L. Bascomb, Jr.

[57] ABSTRACT

A process is provided for the recovery of organic acids from dilute aqueous solutions. The acid in the form of its calcium salt is treated with a tertiary amine carbonate and the resulting trialkylammonium salt of the acid is isolated and heated to give the acid plus a tertiary amine.

19 Claims, No Drawings

RECOVERY OF ORGANIC ACIDS FROM A FERMENTATION BROTH

This is a continuation-in-part of copending application Ser. No. 314,627, filed Oct. 26, 1981 now U.S. Pat. No. 4,405,717.

FIELD OF THE INVENTION

This invention relates to a method for the extraction of organic acids from a dilute aqueous solution in which the acids are present in the form of their calcium salts.

BACKGROUND OF THE INVENTION

The production of various organic acids by microorganisms is well known to those familiar with the fermentation art. These acids are produced by the microorganisms in dilute aqueous solutions so that their recovery in pure form involves separation from a large quantity of water. The expense of such separation has been so great that the production of these acids by fermentation has usually not been able to compete with the production of the acids based on petroleum fossil fuel sources. However, the gradual depletion of petroleum fossil fuel with the resultant increase in prices of petrochemical feedstocks has revived interest in such fermentation reactions which can convert carbohydrates that are renewable raw materials into organic acids and other simple organic chemicals.

When an acid is made by fermentation, the acid formed soon lowers the pH of the medium to a point at which the microorganism no longer grows, and acid production eventually stops. For this reason, it is necessary to add a reagent to the fermentation reaction which will neutralize at least a part of the acid and maintain the pH at a high enough level to permit continued growth of the microbe. The solution must then be acidified before the acid is extracted. The neutralization and acidification steps add to the cost of the process and produce salts which must be disposed of.

It would be of considerable economic importance if a low-cost process could be developed for the extraction of the acid produced by such fermentation reactions. It would be an added benefit if the reagent needed to adjust the pH in the fermentation reaction could be recovered for reuse in the process.

Daniel, et al, in British Pat. No. 1,426,018, published Feb. 25, 1976, disclose a process for the recovery of an acid from an aqueous solution. The extractant is a mixture of an amine which contains at least 20 carbon atoms per molecule and a water-immiscible organic solvent. In order to obtain the acid, it is necessary to back-extract the acid from the organic solvent with water. The resultant solution still contains a large percentage of water and only a partial concentration of the acid is accomplished by this procedure.

A review of the methods of extraction of acetic acid from water is given by C. J. King in the proceedings of the International Solvent Extraction Conference, Series 2, Paper 80-66 (1980). This review includes a summary of the following three references which report work carried out in King's laboratory:

Wardell, et al, J. Chem. Eng. Data, 23, 144 (1978).
Ricker, et al, J. Separ. Proc. Technol., 1 (1) 36–41 (1979).
Ricker, et al, J. Separ. Proc. Technol., 1 (2) 23–33 (1980).

King discloses the extraction of acetic acid from dilute aqueous solutions using various solvent systems. The best solvent systems were mixtures of a high molecular weight tertiary amine or a trialkyl phosphine oxide diluted with a polar solvent. The preferred solvent was a mixture of a commercial amine, consisting largely of trioctylamine, and diisopropyl ketone. The use of tributylamine was dismissed because the tributylamine-acetic acid complex was too soluble in water for this amine to be satisfactory for the extraction.

A convenient method for the extraction of organic acids has now been discovered. This process does not require prior acidification of the fermentation broth and permits the use of solvents previously considered to be unsuitable for the extraction. Furthermore, the reagent needed for maintaining the pH in the fermentation broth is recovered for reuse in the process.

SUMMARY OF THE INVENTION

In accordance with the present invention, there is provided a process for the recovery of an organic acid selected from the group consisting of propionic acid, butyric acid, lactic acid and citric acid, from a fermentation reaction which comprises:
  (a) converting of the acid to its calcium salt,
  (b) adding a molar equivalent of a water-soluble tertiary amine carbonate to the calcium salt solution to form the trialkylammonium salt of the acid in solution and a precipitate of calcium carbonate;
  (c) concentrating the trialkylammonium salt solution; and
  (d) heating the concentrated trialkylammonium salt solution to obtain the acid and the tertiary amine.

Also, in accordance with the invention, there is provided a process for the recovery of an organic acid selected from the group consisting of propionic acid, butyric acid, lactic acid and citric acid, from an aqueous solution of its calcium salt which comprises the steps of:
  (a) adding a molar equivalent of a water-soluble tertiary amine carbonate to the calcium salt solution to form the trialkylammonium salt of the acid in solution and a precipitate of calcium carbonate;
  (b) concentrating the trialkylammonium salt solution; and
  (c) heating the concentrated trialkylammonium salt solution to obtain the acid and the tertiary amine.

DETAILED DESCRIPTION OF THE INVENTION

The process of this invention can be used to extract an acid from a dilute solution of the acid. It is particularly suitable for extraction of acid from solutions which contain the acid in the form of its calcium salt. Such solutions are obtained from acid-producing fermentation reactions in which the pH is maintained in the range of from about 4.5 to about 7.0 by the addition of calcium carbonate or calcium hydroxide. The concentration of the acid, or its calcium salt, in the solution can vary over a wide range, but is usually less than about 10% by weight.

In carrying out the process of this invention, a molar equivalent of a water-soluble tertiary amine carbonate is added to the calcium salt solution. The tertiary amine carbonate used in the process can be generated by the addition of carbon dioxide to a solution or suspension of the tertiary amine in water. It is most convenient to generate the tertiary amine carbonate in situ by first adding a molar equivalent of the tertiary amine to the calcium salt solution. Then carbon dioxide is added to the mixture to generate the tertiary amine carbonate directly in the calcium salt solution. The addition of the carbon dioxide is carried out by any convenient means. Either solid or gaseous carbon dioxide is added to the solution at atmospheric pressure or at higher pressures in a pressure vessel.

The amines used in the process of this invention are preferably tertiary amines. Primary and secondary amines tend to form amides with organic acids under the conditions of the process, and for this reason, are less satisfactory. Any tertiary amine which forms a water-soluble carbonate with carbon dioxide under the conditions of the process can be used. Preferred amines are those which do not form azeotropes with the acid and which distill at a temperature sufficiently different from the distillation temperature of the acid to permit separation of the acid from a mixture of the acid and the amine by fractional distillation. The amine should be sufficiently stable on heating so that it does not undergo decomposition when the trialkylammonium salt is heated in the final step of the process.

The lower molecular weight tertiary amines, trimethylamine, triethylamine and tripropylamine, form carbonates which are water soluble. However, these amines may form azeotropes with some of the acids or tend to codistill with them. The higher symmetrical amines, such as trihexylamine and trioctylamine, do not form carbonates which are sufficiently soluble in water. Higher molecular weight tertiary amines, in which one of the alkyl groups is methyl or ethyl, do form water-soluble carbonates, but they may tend to undergo decomposition when heated to a temperature sufficient to decompose their acid salts in the last step of the process.

The tertiary amines, dicyclohexylmethylamine and tributylamine, are suitable when higher boiling amines are desired for use in this process. Tributylamine is preferred. This amine dissolves readily when carbon dioxide is added to a mixture of the amine in various dilute calcium salt solutions. Furthermore, tertiary butylamine has a sufficiently high boiling point so that it does not distill at a temperature at which tributylammonium salts of some of the acids readily dissociate with the organic acid distilling from the mixture.

When a water-soluble tertiary amine carbonate is mixed with the calcium salt solution, a precipitate of calcium carbonate is formed. It is preferable to separate this salt before the trialkylammonium salt is extracted from the solution. Separation is accomplished by standard procedures such as filtration or centrifugation. When the process is used to recover organic acids from a fermentation reaction, the calcium carbonate can be reused to maintain the pH of the fermentation medium in the desired range. By this procedure, the acid produced in the fermentation reaction is converted to its calcium salt as it is produced by the microorganism.

The mixture of amine and acid, which is present in the solution, is designated herein as a trialkylammonium salt. This phrase includes the combination of amine and acid in whatever form it occurs in solution. The combination may be a salt, a complex, or mixtures of these with the free amine and free acid.

In one embodiment of this invention, the trialkylammonium salt may be extracted from the solution by means of an organic solvent. Polar solvents, such as esters, alcohols, ketones, ethers or chlorinated hydrocarbons may be used. The solvents should be insoluble or sparingly soluble in water and be good extractants for the trialkylammonium salt. This extraction ability is determined by measuring the amount of acid in each phase when the salt solution is extracted with an equal volume of extractant. The extraction ability is expressed as a Distribution Coefficient ($K_D$) which is defined by the formula:

$$K_D = \frac{\text{grams acid in organic phase/grams organic phase}}{\text{grams acid in aqueous phase/grams aqueous phase}}$$

The solvent should have a $K_D$ greater than about 0.4 and preferably greater than about 1.

The organic solvent used in this invention should be one that does not react with the acid under the conditions of the process. The solvent is preferably one having a boiling point sufficiently low so that it distills from a mixture of the solvent and trialkylammonium salt below the temperature at which the salt decomposes. Furthermore, the solvent should not form an azeotrope with the acid. Chloroform is the preferred organic solvent for use in the process of this invention when the amine employed is tributylamine.

Methods other than solvent extraction can be used to concentrate the trialkylammonium salt. These include evaporation of water from the salt solution and freeze crystallization of the salt.

In the final step of the process, the trialkylammonium salt is heated to cause dissociation of the salt with liberation of the acid and the amine. The temperature at which the trialkylammonium salt decomposes depends somewhat on the tertiary amine and acid. Either the tertiary amine or the acid is distilled from the mixture, depending on their relative boiling points.

Thus, it is apparent that there has been provided, in accordance with the invention, a process for the recovery of organic acids from a solution in which the acid is in the form of its calcium salt. It is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the recovery of an organic acid selected from the group consisting of propionic acid, butyric acid, lactic acid and citric acid, from an aqueous solution of its calcium salt which comprises the steps of:
    (a) adding a molar equivalent of a water-soluble tertiary amine carbonate to the calcium salt solution to form a trialkylammonium salt of the acid in solution and a precipitate of calcium carbonate;
    (b) concentrating the trialkylammonium salt solution; and
    (c) heating the concentrated trialkylammonium salt solution to obtain the acid and the tertiary amine.

2. The process of claim 1 wherein the tertiary amine is tributylamine.

3. The process of claim 1 wherein the tertiary amine is dicyclohexylmethylamine.

4. The process of claim 1 wherein the trialkylammonium salt is concentrated by extraction with a solvent.

5. The process of claim 4 wherein the precipitated calcium carbonate is separated from the solution of trialkylammonium salt before said salt is extracted with a solvent.

6. The process of claim 4 wherein the solvent is chloroform.

7. The process of claim 4 wherein the solvent is distilled from the extract of trialkylammonium salt before the salt is heated to obtain the acid and the tertiary amine.

8. The process of claim 1 wherein the tertiary amine carbonate used in Step (a) is generated in situ by first adding to the solution of the calcium salt of the acid a molar equivalent of a tertiary amine that forms a water-soluble carbonate and then adding sufficient carbon dioxide to dissolve the amine and to precipitate the calcium as calcium carbonate.

9. The process of claim 1 wherein the tertiary amine obtained in Step (c) is converted to a tertiary amine carbonate and recycled to Step (a).

10. A process for the recovery of an organic acid, selected from the group consisting of propionic acid, butyric acid, lactic acid and citric acid, from a fermentation reaction which comprises:
  (a) converting of the acid to its calcium salt;
  (b) adding a molar equivalent of a water-soluble tertiary amine carbonate to the calcium salt solution to form the trialkylammonium salt of the acid in solution and a precipitate of calcium carbonate;
  (c) concentrating the trialkylammonium salt solution; and
  (d) heating the concentrated trialkylammonium salt solution to obtain the acid and the tertiary amine.

11. The process of claim 10 wherein the tertiary amine carbonate used in Step (b) is generated in situ by first adding to the calcium salt solution a molar equivalent of a tertiary amine that forms a water-soluble carbonate and then adding sufficient carbon dioxide to dissolve the amine and to precipitate the calcium as calcium carbonate.

12. The process of claim 10 wherein the tertiary amine obtained in Step (d) is converted to a tertiary amine carbonate and recycled to Step (b).

13. The process of claim 10 wherein the calcium carbonate obtained in Step (b) is added to the fermentation reaction to convert the acid to its calcium salt.

14. The process of claim 10 wherein the tertiary amine is tributylamine.

15. The process of claim 10 wherein the tertiary amine is dicyclohexylmethylamine.

16. The process of claim 10 wherein the trialkylammonium salt is concentrated by extraction with a solvent.

17. The process of claim 16 wherein the solvent is distilled from the extract of trialkylammonium salt before the salt is heated to obtain the acid and the tertiary amine.

18. The process of claim 16 wherein the precipitated calcium carbonate is separated from the solution of trialkylammonium salt before said salt is extracted with a solvent.

19. The process of claim 16 wherein the solvent is chloroform.

* * * * *